United States Patent
Richard

(10) Patent No.: US 8,025,867 B2
(45) Date of Patent: *Sep. 27, 2011

(54) PHOTOPROTECTIVE COSMETIC COMPOSITIONS COMPRISING PHOTOSTABILIZED DIBENZOYLMETHANE COMPOUNDS AND MEROCYANINE SULFONE COMPOUNDS

(75) Inventor: Herve Richard, Les Pavillons Sous Bois (FR)

(73) Assignee: L'Oreal, Paris (FR)

( * ) Notice: Subject to any disclaimer, the term of this patent is extended or adjusted under 35 U.S.C. 154(b) by 515 days.

This patent is subject to a terminal disclaimer.

(21) Appl. No.: 11/987,111

(22) Filed: Nov. 27, 2007

(65) Prior Publication Data

US 2008/0305058 A1    Dec. 11, 2008

Related U.S. Application Data

(63) Continuation of application No. PCT/EP2006/005332, filed on May 15, 2006.

(60) Provisional application No. 60/690,502, filed on Jun. 15, 2005.

(30) Foreign Application Priority Data

May 27, 2005  (FR) ...................... 05 51398

(51) Int. Cl.
- A61K 8/00 (2006.01)
- A61K 8/18 (2006.01)
- A61Q 17/04 (2006.01)
- C03C 25/24 (2006.01)
- C07F 7/18 (2006.01)

(52) U.S. Cl. ................ 424/59; 424/60; 424/70.9; 556/9

(58) Field of Classification Search ................ None
See application file for complete search history.

(56) References Cited

U.S. PATENT DOCUMENTS

| | | | |
|---|---|---|---|
| 4,195,999 A * | 4/1980 | Adachi et al. | 430/507 |
| 6,426,428 B2 | 7/2002 | Forestier et al. | |
| 6,627,179 B2 * | 9/2003 | Candau | 424/59 |
| 7,510,703 B2 * | 3/2009 | Richard | 424/59 |

FOREIGN PATENT DOCUMENTS

| | | | |
|---|---|---|---|
| EP | 0709080 B1 | 5/1996 | |
| EP | 0868905 A2 | 10/1998 | |
| WO | WO 2004/006878 A1 | 1/2004 | |
| WO | WO 2004/075871 A1 | 9/2004 | |

* cited by examiner

*Primary Examiner* — Carlos Azpuru
*Assistant Examiner* — David Browe
(74) *Attorney, Agent, or Firm* — Buchanan Ingersoll & Rooney PC

(57) ABSTRACT

Photostable, topically applicable cosmetic/dermatological compositions contain at least one dibenzoylmethane compound UV-A sunscreen and at least one merocyanine sulfone compound.

26 Claims, No Drawings

PHOTOPROTECTIVE COSMETIC COMPOSITIONS COMPRISING PHOTOSTABILIZED DIBENZOYLMETHANE COMPOUNDS AND MEROCYANINE SULFONE COMPOUNDS

CROSS-REFERENCE TO PRIORITY/PCT/PROVISIONAL APPLICATIONS

This application claims priority under 35 U.S.C. §119 of FR 05/51398, filed May 27, 2005, and of Provisional Application No. 60/690,502, filed Jun. 15, 2005, and is a continuation of PCT/EP 2006/005332, filed May 15, 2006 and designating the United States, published in the English language as WO 2006/125676 A1 on Nov. 30, 2006, each hereby expressly incorporated by reference in its entirety and each assigned to the assignee hereof.

BACKGROUND OF THE INVENTION

1. Technical Field of the Invention

The present invention relates to photostabilizing at least one dibenzoylmethane derivative against UV radiation employing at least one merocyanine sulfone derivative.

This invention also relates to novel compositions, in particular cosmetic compositions for topical application.

2. Description of Background and/or Related and/or Prior Art

Light radiation with wavelengths in the range 280 nm to 400 nm is known to brown the human epidermis; more particularly, rays with a wavelength in the range 280 to 320 nm, known as UV-B, are known to cause erythema and cutaneous burns which may be deleterious to the development of a natural tan. For those and for aesthetic reasons, there is a constant demand for means for controlling natural tanning which can thereby control the color of the skin; thus, UV-B radiation must therefore be screened.

It is also known that UV-A rays with wavelengths in the range 320 to 400 nm, which cause the skin to brown, tend to induce an impairment therein, in particular with sensitive skin or skin which is continually exposed to solar radiation. In particular, UV-A radiation causes the skin to lose elasticity and the appearance of wrinkles, resulting in premature aging of the skin. The radiation encourages triggering the erythematous reaction or amplifies that reaction in certain subjects and may even be the cause of phototoxic or photo-allergic reactions. Hence, for aesthetic and cosmetic reasons, such as preserving the natural elasticity of the skin, for example, more and more individuals seek to control the effect of UV-A radiation on their skin. Thus, screening UV-A radiation is also desirable.

With the goal of ensuring protection of the skin and keratinous substrates against UV radiation, sunscreen compositions are generally used which comprise organic screens which are active in the UV-A and active in the UV-B regions. The majority of such screens are liposoluble.

In this respect, a current particularly advantageous family of UV-A screens is constituted by dibenzoylmethane derivatives, in particular 4-tert-butyl-4'-methoxydibenzoyl methane, which have intrinsically good absorbing powers. Such dibenzoylmethane derivatives, which are now well known per se as screens which are active in the UV-A region, have been described in FR-A-2,326,405 and FR-A-2,440,933, as well as in EP-A-0,114,607; 4-tert-butyl-4'-methoxydibenzoyl methane is currently marketed under the trademark "Parsol 1789" by ROCHE VITAMINS.

Unfortunately, it has been discovered that dibenzoylmethane derivatives are relatively sensitive to ultraviolet radiation (in particular UV-A), i.e., more precisely, they have an annoying tendency to degrade at a greater or lesser rate under the action thereof. This substantial lack of photochemical stability of dibenzoylmethane derivatives to the ultraviolet radiation to which they are by their very nature intended to be subjected cannot guarantee constant protection during prolonged exposure to the sun, and repeated applications at regular, close intervals have to be made by the consumer to effectively protect the skin against UV radiation.

SUMMARY OF THE INVENTION

It has now surprisingly been discovered that by combining an effective quantity of a merocyanine sulfone derivative, notably those having a particular formula, with the dibenzoylmethane derivatives mentioned above, it is possible to substantially and remarkably improve the photochemical stability (or photostability) of those dibenzoylmethane derivatives.

This essential discovery forms the basis of the present invention.

Thus, the present invention features a method for improving the stability of at least one dibenzoylmethane compound against UV radiation, which comprises combining at least one merocyanine sulfone compound with said dibenzoylmethane compound.

The present invention also features cosmetic or dermatological compositions for topical application, comprising formulating at least the following, into a cosmetically acceptable support:

(a) at least one UV screen of the dibenzoylmethane derivative type; and (b) at least one merocyanine sulfone derivative.

The present invention also features to the use of at least one merocyanine sulfone derivative as a photostabilizing agent for UV screens of the dibenzoylmethane derivative type.

Finally, the present invention also features the formulation of a merocyanine sulfone derivative into a cosmetic or dermatological composition comprising at least one UV screen of the dibenzoylmethane derivative type to improve the stability of said dibenzoylmethane derivative to UV radiation.

Other characteristics, aspects and advantages of the invention will become apparent from the following detailed description.

Throughout the present description, the term "system screening UV radiation" means an agent screening UV radiation constituted either by a single UV radiation-screening organic or mineral compound or a mixture of several UV radiation-screening organic or mineral compounds, for example a mixture comprising a UV-A screen and a UV-B screen.

DETAILED DESCRIPTION OF BEST MODE AND SPECIFIC/PREFERRED EMBODIMENTS OF THE INVENTION

Exemplary dibenzoylmethane compounds according to the invention include:

2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;

4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane;
2,6-dimethyl-4-tert-butyl-4'-methoxydibenzoylmethane.

Of the dibenzoylmethane derivatives indicated above, 4-isopropyl-dibenzoylmethane is particularly preferred, marketed under the trademark "EUSOLEX 8020" by MERCK, having the following formula:

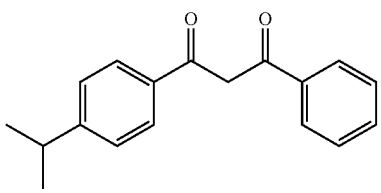

More particularly, 4-(tert-butyl)-4'methoxy dibenzoylmethane or Butyl Methoxy Dibenzoylmethane, marketed under the trademark "PARSOL 1789" by Roche Vitamins is also preferred; this screen has the following formula:

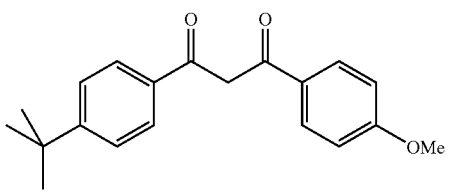

The dibenzoylmethane derivative or derivatives may be present in the compositions in accordance with the invention in amounts which preferably vary from 0.01% to 10% by weight and more preferably from 0.1% to 6% by weight with respect to the total composition weight.

Exemplary merocyanine sulfone derivatives of the present invention are those having one or another of the following formulae (1) to (3):

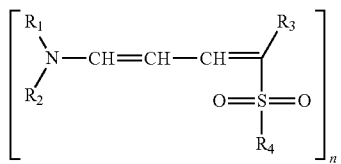 (1)

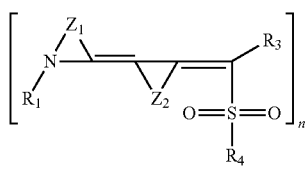 (2)

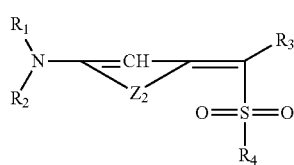 (3)

in which:

$R_1$ and $R_2$, which may be identical or different, are each H, a $C_1$-$C_{22}$ alkyl radical, a $C_3$-$C_8$ cycloalkyl radical, a $C_6$-$C_{20}$ aryl radical, with the proviso that only one of $R_1$, $R_2$ is H and that $R_1$ and $R_2$ may together form, with the nitrogen from which they depend, a cycle containing the —$(CH_2)_m$— group, which may be uninterrupted or interrupted by —O— or by —NH—;

$R_3$ is a carboxyl group, —$COOR_5$, —$CONHR_5$, —$COR_5$, —$CONR_1R_5$, —CN or —$SO_2R_5$;

$R_4$ and $R_5$, which may be identical or different, are each a $C_1$-$C_{22}$ alkyl radical, a $C_3$-$C_8$ cycloalkyl radical or a $C_6$-$C_{20}$ aryl radical;

$Z_1$ and $Z_2$, which may be identical or different, are —$(CH_2)_m$— groups which may be uninterrupted or interrupted by —O—, —S— or —$NR_6$— and/or which may be unsubstituted or substituted with a $C_1$-$C_6$ alkyl radical;

$R_6$ is a $C_1$-$C_5$ alkyl radical;

l is 1-4;

m is 1-7;

n is 1-4;

with the proviso that:

(i) when n=2, $R_1$, $R_4$ or $R_5$ is an alkyl di-radical or $R_1$ and $R_2$ together form with 2 nitrogen atoms, a divalent —$(CH_2)_m$— radical;

(ii) when n=3, $R_1$, $R_4$ or $R_5$ are a trivalent radical;

(iii) when n=4, $R_1$, $R_4$ or $R_5$ are a tetravalent radical; and (iv) $R_1$ and $R_2$ are not simultaneously a hydrogen atom.

The compounds of formula (1) may be in their E,E-, E,Z- or Z,Z-isomeric forms.

Of these three families of compounds, compounds having formula (1) are preferred.

Particularly preferred compounds of formula (1) are those for which the following conditions are satisfied:

$R_1$ and $R_2$, which may be identical or different, designate $C_1$-$C_{12}$ alkyl radical;

$R_3$ designates a $COOR_5$ group;

$R_4$ designates a phenyl or tolyl group;

$R_5$ designates $C_1$-$C_{12}$ alkyl;

n equals 1 or 2.

Examples of particularly preferred compounds of formula (1) are those having the following formulae (a) to (d):

Ethyl 5-(dihexylamino)-2-(phenylsulfonyl)-2,4-pentadienoate:

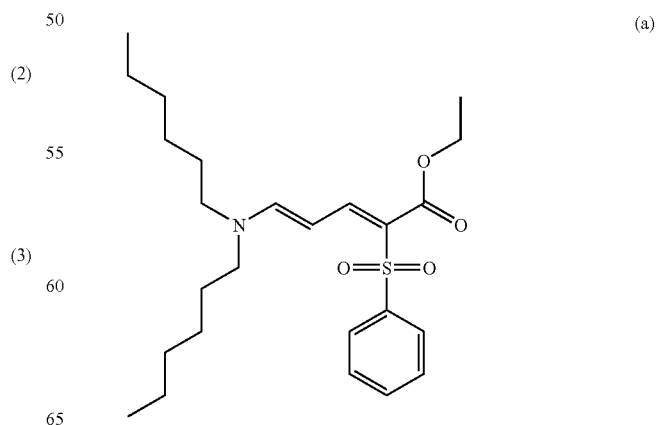 (a)

Octyl 5-N,N-diethylamino-2-phenylsulfonyl-2,4-pentadienoate:

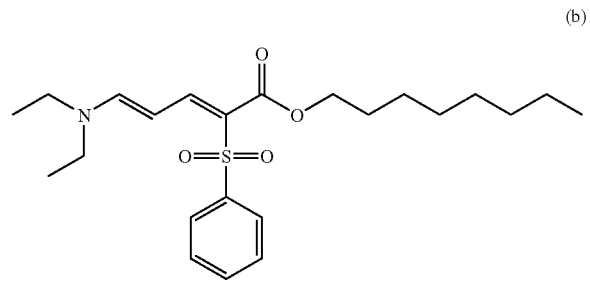

Lauryl 5-N,N-diethylamino-2-phenylsulfonyl-2,4-pentadienoate:

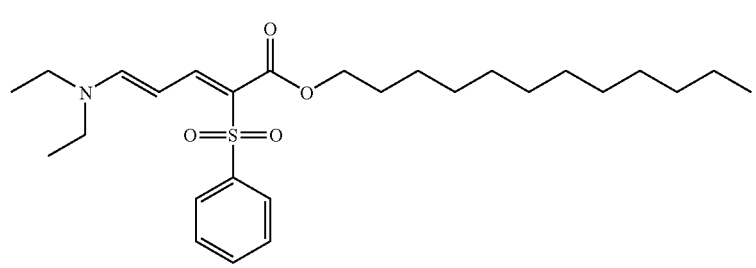

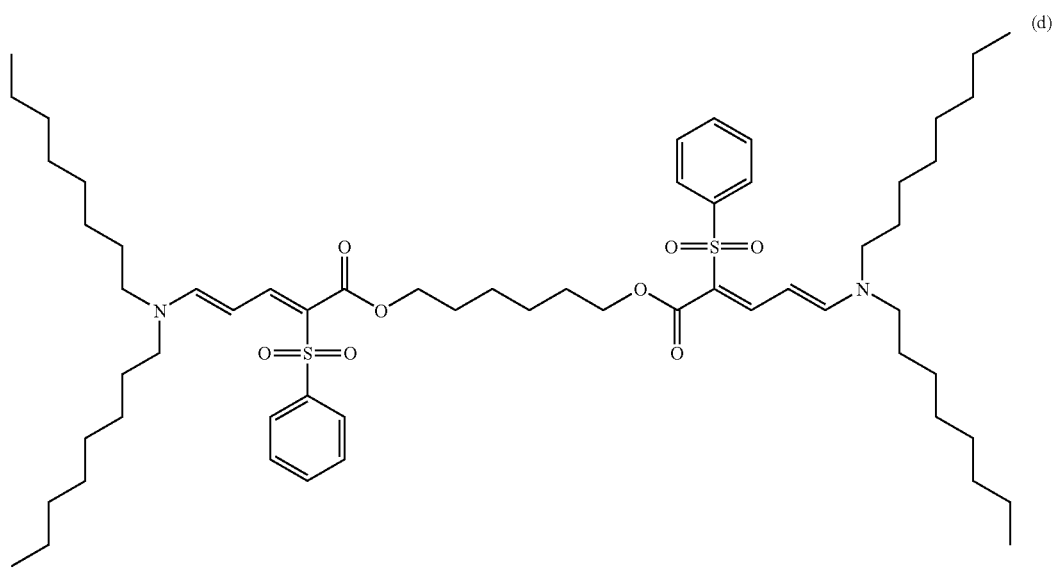

Syntheses for derivatives of formulae (1) to (3) have been described in U.S. Pat. Nos. 2,186,608, 3,723,154, 4,045,229, 4,195,999, EP-0,127,819, EP-0,210,409, WO 2004/006878 and IPCOM000022279D.

Merocyanine sulfone derivative compounds in accordance with the present invention which may also be cited are those having one or another of the following formulae (4) to (6):

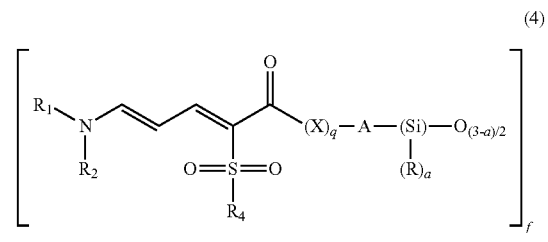

-continued

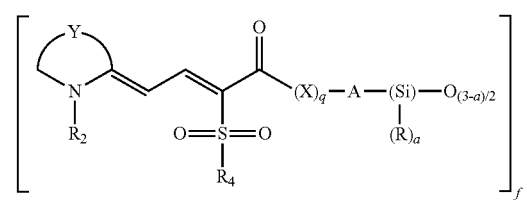

-continued

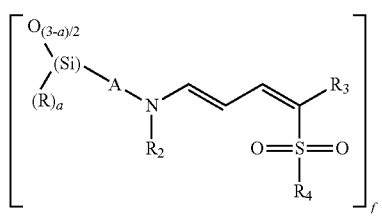
(6)

in which:

X is —O—, —NR$_5$—;
wherein R$_1$, R$_2$, R$_3$, R$_4$ are as defined in formulae (1), (2) and (3) above;
o=0 or 1;
q=0 or 1;
Y is a divalent C$_1$-C$_5$ alkyl radical, optionally substituted with C$_1$-C$_4$ alkyl radicals and/or containing —O—, —S— atoms, or with an —NR$_1$, group;
the radicals R, which may be identical or different, are each a linear or branched C$_1$-C$_{20}$ alkyl radical which may optionally be halogenated, a C$_6$-C$_{12}$ aryl radical or a C$_1$-C$_{10}$ alkoxy group;
a=0 to 3;
A is a divalent radical selected from among methylene, ethylene or a group having one of the following formulae (7), (8) or (9):

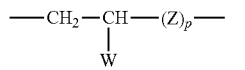
(7)

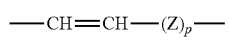
(8)

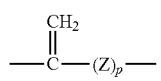
(9)

in which:

Z is a linear or branched, saturated or unsaturated C$_1$-C$_6$ alkylene radical, optionally substituted with a hydroxyl radical or a linear or branched, saturated or unsaturated C$_1$-C$_8$ alkyl radical;
W is a hydrogen atom; a hydroxyl radical or a linear or branched, saturated or unsaturated C$_1$-C$_8$ alkyl radical;
p is 0 or 1;
f=1 or 2.

The compounds of formulae (4), (5) and (6) may be present in the E,E-, E,Z- or Z,Z-isomeric forms.

In addition to units with formula -A-(Si)(R)$_a$(O)$_{(3-a)/2}$, the organosiloxane may comprise units with formula (R)$_b$—(Si)(O)$_{(4-b)/2}$ in which:
R is as defined in formulae (1) to (3);

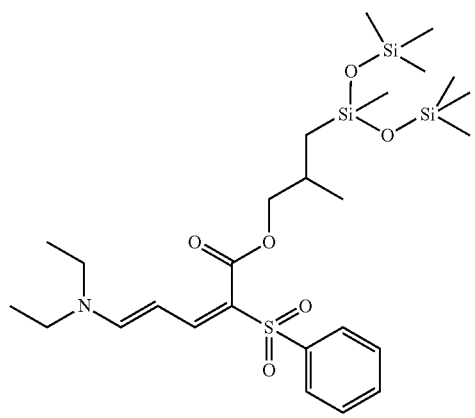
(e)

b=1, 2 or 3.

Preferably, the —(Si)(R)$_a$(O)$_{(3-a)/2}$ groups may be represented by the following formulae (10), (11) or (12):

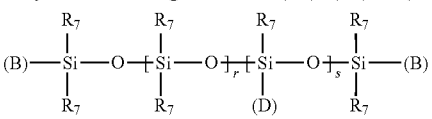
(10)

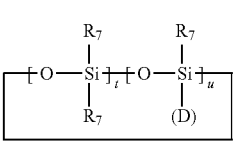
(11)

(D)—Si(R$_7$)$_3$
(12)

in which:

D binds the silicone chain of group A to chromophores with formulae (4) to (6);
the radicals R$_7$, which may be identical or different, are each selected from among linear or branched C$_1$-C$_{30}$ alkyl, phenyl, 3,3,3-trifluoropropyl and trimethylsilyloxy radicals, at least 80% by number of radicals R$_7$ being methyl;
the radicals (B), which may be identical or different, are each selected from among radicals R$_8$ and radical A;
r is a whole number ranging from 0 to 200 inclusive, and s is a whole number ranging from 0 to 50 inclusive, and if s=0, at least one of the two symbols (B) designates A;
u is a whole number ranging from 1 to 10 inclusive, and t is a whole number ranging from 0 to 10 inclusive, with the proviso that t+u equals 3 or more.

In formulae (1) to (7) above, the alkyl radicals may be linear or branched, saturated or unsaturated, and in particular selected from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl. The methyl radical is the particularly preferred alkyl radical.

In formulae (1) to (7) above, the aryl radicals are preferably selected from phenyl and tolyl.

More particularly, Y is a group of atoms which results in the formation of an oxazolidine cycle, a pyrrolidine cycle, a thiazolidine cycle or an indoline bi-cycle.

Linear or cyclic diorganosiloxanes of formula (10) or (11) according to the present invention are random oligomers or polymers preferably having at least one and more preferably all of the following characteristics:

R$_8$ is preferably methyl;
B is preferably methyl (case of linear compounds of formula (10)).

Particularly preferred examples of compounds of formula (4) are those having the following formulae (e) to (i):

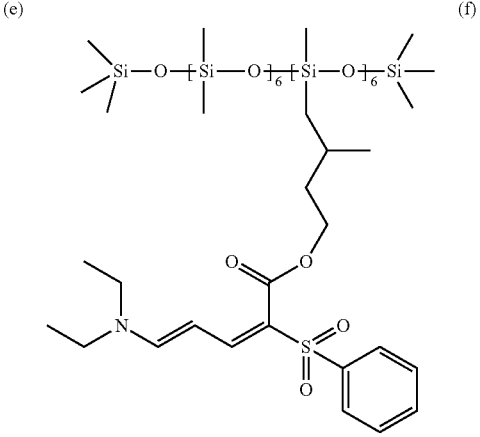
(f)

-continued
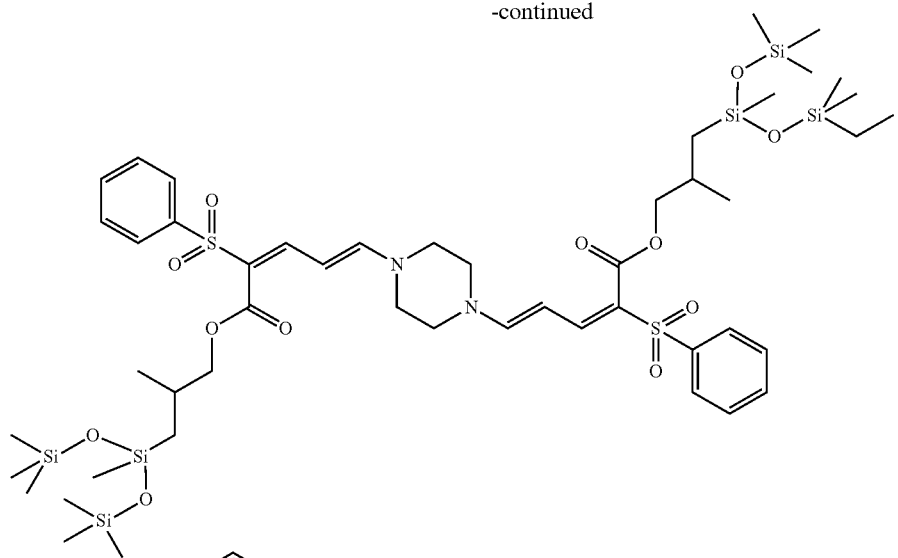
(g)
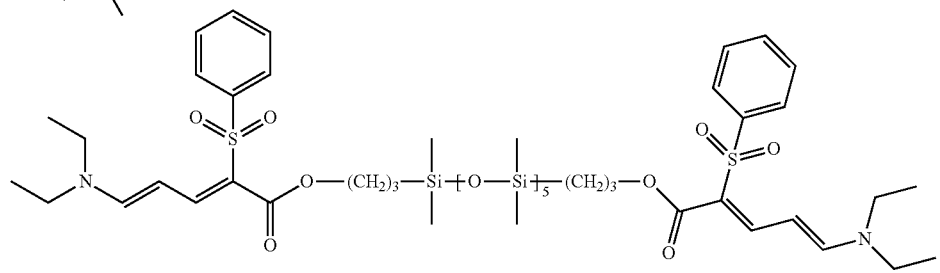
(h)
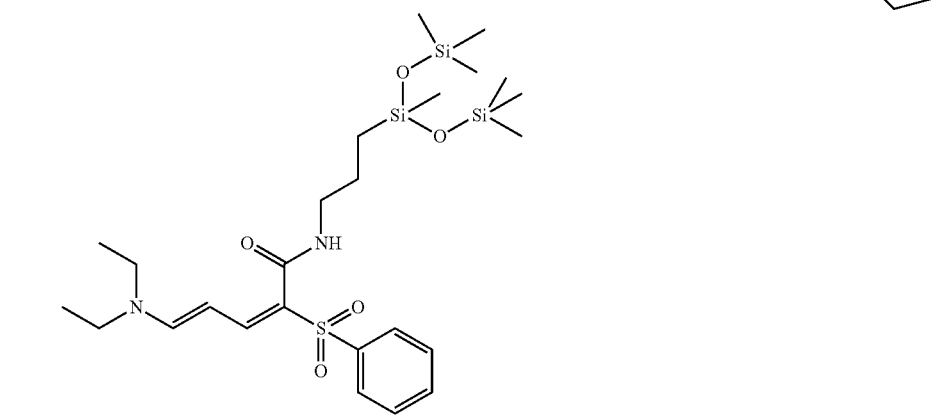
(i)
Particularly preferred examples of compounds of formula (5) are the mixture of compounds having the following formula (j):
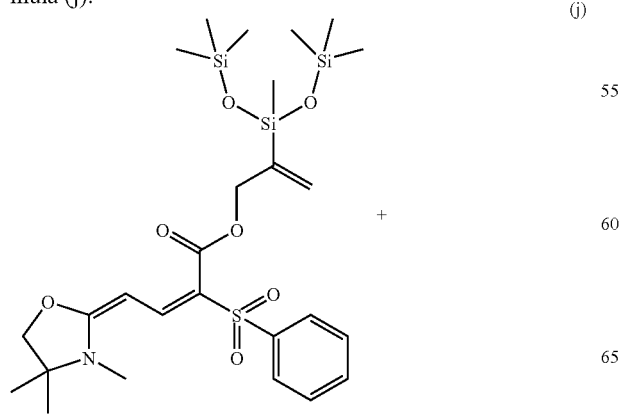
(j)
+
-continued
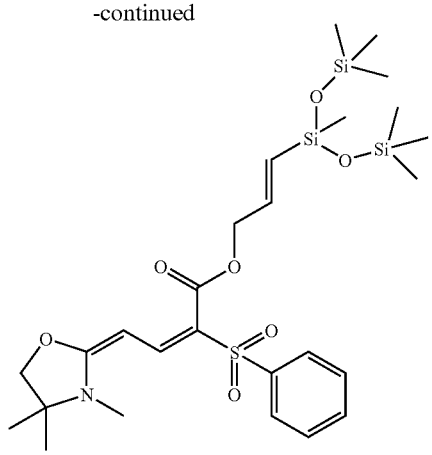

Particularly preferred examples of compounds of formula (6) are compounds having the following formulae (k) to (p):
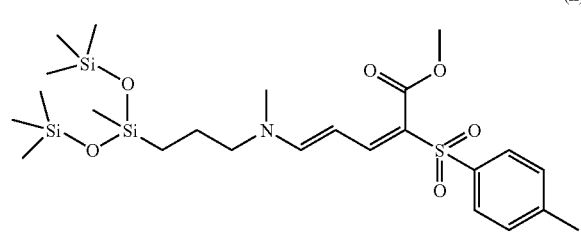
(k)
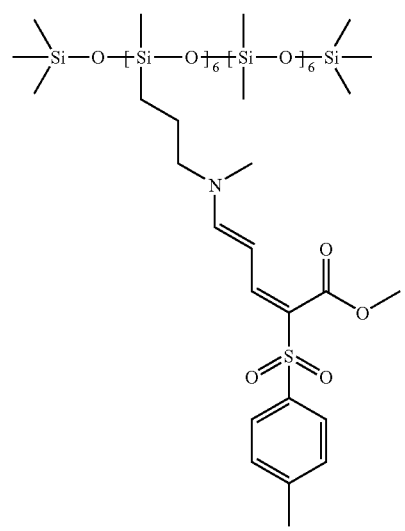
(l)
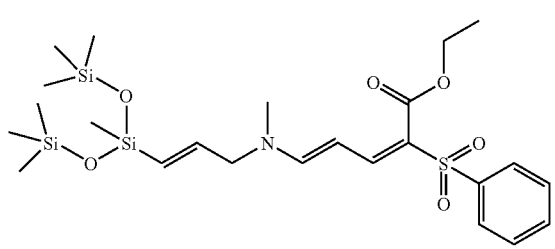
(m)
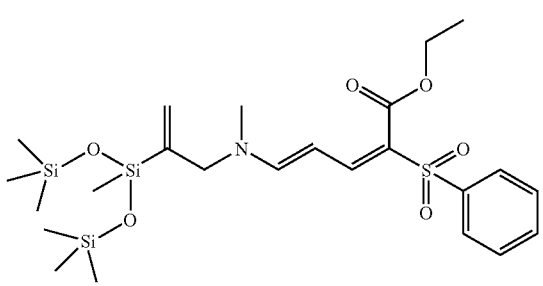
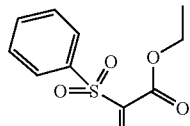
(n)
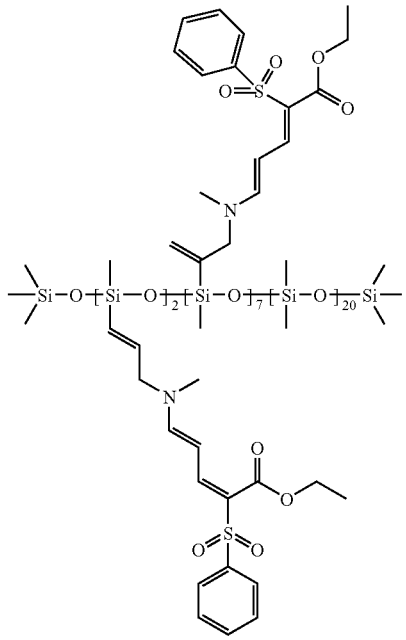
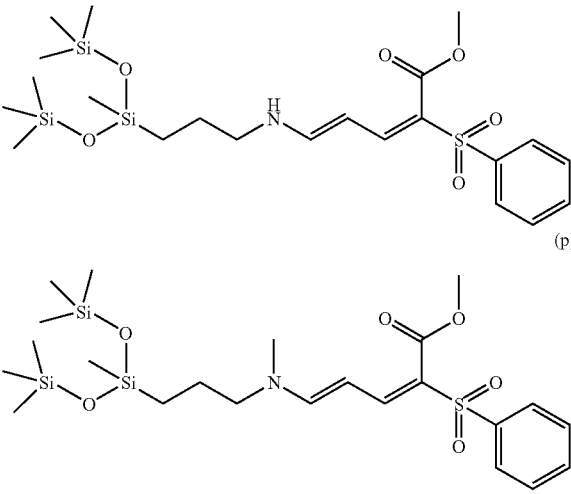
(o)
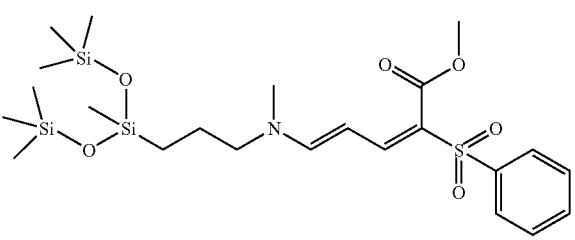
(p)
The derivatives of formula (4) may be prepared utilizing a method as described in U.S. Pat. Nos. 4,045,229 and 4,195,999 in accordance with the following reaction scheme:
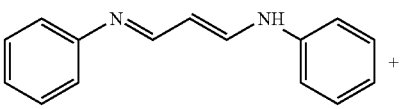
(13)
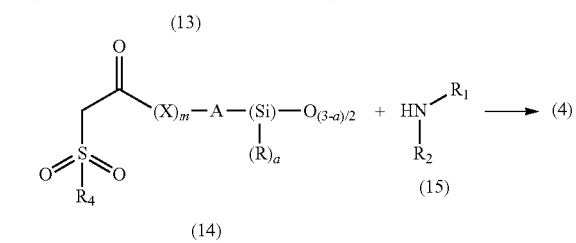
(14)    (15)    → (4)

in which radicals R, $R_1$, $R_2$, $R_3$, A, X, a and m have the definitions given in the above formulae.

The derivatives of formula (5) may be prepared utilizing a method described in WO 0020388 in accordance with the following reaction scheme:

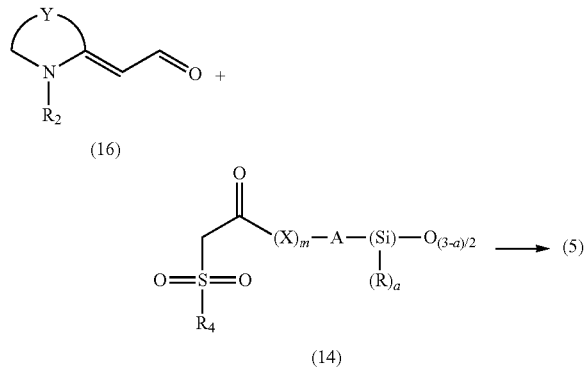

in which radicals R, $R_1$, $R_2$, A, X, Y, a and m have the definitions given in the above formulae.

The derivatives of formula (6) may be prepared utilizing a method described in U.S. Pat. Nos. 4,045,229 and 4,195,999 in accordance with the following reaction scheme:

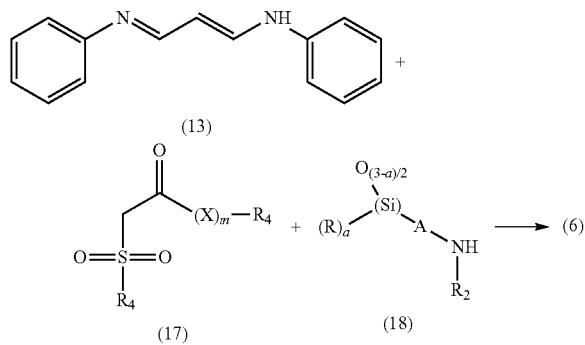

in which radicals R, $R_1$, $R_2$, $R_4$, A, X, a and m have the definitions given in the above formulae.

Compounds of formula (14) may be obtained conventionally employing a hydrosilylation reaction starting from a siloxane or silane derivative of formulae (10) to (12) in which, for example, all of (D) are hydrogen atoms (this derivative is hereinafter denoted the SiH derivative) and an unsaturated derivative, in accordance with the following reaction scheme:

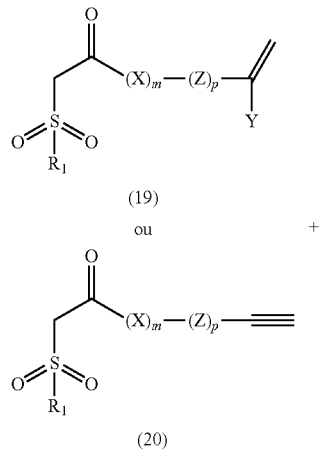

-continued

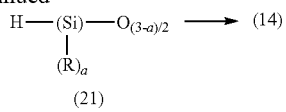

in which radicals R, $R_1$, A, X, Y, Z, a, m and p have the definitions given in the above formulae.

The SiH groups may be present in the chain and/or at the chain ends. Said SiH derivatives are products which are well known in the silicone industry and are generally commercially available. They have been described, for example, in U.S. Pat. Nos. 3,220,972, 3,697,473 and 4,340,709.

In a similar manner, the derivatives of formula (18) may be obtained in accordance with the following reaction scheme:

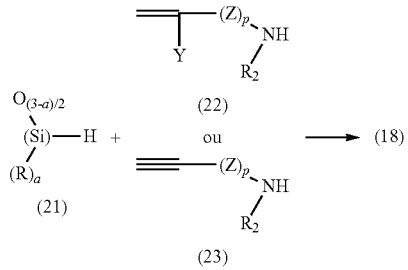

in which radicals R, $R_2$, Y, Z and p have the definitions given in the above formulae.

Merocyanine sulfone compounds in accordance with the invention are preferably present in the subject compositions in amounts of 0.01% to 20% by weight, more preferably 0.1% to 10%, more preferably 0.1% to 6% by weight with respect to the total composition weight.

According to the present invention, the merocyanine sulfone derivative or derivatives will be used in a quantity sufficient to obtain a substantial and significant improvement in the photostability of the dibenzoylmethane derivative in a given composition. This minimum quantity of photostabilizing agent to be used may vary depending on the starting quantity of dibenzoylmethane present in the composition and depending on the nature of the cosmetically acceptable support used in the composition. It may be determined without difficulty using a conventional photostability measuring test.

The compositions according to the invention are generally suited for topical application to the skin and thus generally comprise a physiologically acceptable medium, i.e., compatible with the skin and/or integuments (hair, eyelashes, eyebrows, nails). Preferably, it is a cosmetically acceptable medium, i.e., with an agreeable color, odor and feel which does not generate unacceptable discomfort (smarting, tightness, redness), which may deter the consumer from using that composition.

The compositions in accordance with the invention will preferably comprise other complementary organic or inorganic photoprotective agents which are active in the UV-A and/or UV-B region, which are hydrophilic or lipophilic or even insoluble in the cosmetic solvents in routine use.

The complementary organic photoprotective agents are selected in particular from anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives, in particular those mentioned in U.S. Pat. No. 5,624,663; benzimidazole derivatives; imidazolines; bis-benzoazolyl derivatives such as those described in EP-0,669,323 and U.S. Pat. No. 2,463,264; p-aminobenzoic acid (PABA) derivatives; methylene bis-(hydroxyphenyl benzotriazole) derivatives as described in U.S. Pat. Nos. 5,237,071, 5,166, 355, GB-2,303,549, DE-197,26,184 and in EP-0,893,119; benzoxazole derivatives as described in EP-0,832,642, EP-1, 027,883, EP-1,300,137 and DE-101,62,844; polymeric screens and silicone screens such as those described in WO 93/04665; dimeric α-alkylstyrene derivatives such as those described in DE-19855649; 4,4-diarylbutadienes as described in E-0,0967200, DE-19746654, DE-19755649, EP-1,008,586, EP-1,133 980 and EP-0,133,981 and mixtures thereof. Examples of complementary organic photoprotective agents which are representative are those designated below under their INCI names:

Para-aminobenzoic Acid Derivatives:
PABA;
Ethyl PABA;
Ethyl Dihydroxypropyl PABA;
Ethylhexyl Dimethyl PABA, marketed in particular under the trademark "ESCALOL 507" by ISP;
Glyceryl PABA;
PEG-25 PABA, marketed under the trademark "UVINUL P25" by BASF;
Salicylic Derivatives
Homosalate, marketed under the trademark "Eusolex HMS" by Rona/EM Industries;
Ethylhexyl Salicylate, marketed under the trademark "NEO HELIOPAN OS" by HAARMANN and REIMER;
Dipropyleneglycol Salicylate, marketed under the trademark "DIPSAL" by SCHER;
TEA Salicylate, marketed under the trademark "NEO HELIOPAN TS" by HMRMANN and REIMER;
Cinnamic Derivatives:
Ethylhexyl Methoxycinnamate, marketed in particular under the trademark "PARSOL MCX" by HOFFMANN LA ROCHE;
Isopropyl Methoxy cinnamate;
Isoamyl Methoxy cinnamate, marketed under the trademark "NEO HELIOPAN E 1000" by HMRMANN and REIMER;
Cinoxate;
DEA Methoxycinnamate;
Diisopropyl Methylcinnamate;
Glyceryl Ethylhexanoate dimethoxycinnamate;
β,β-Diphenylacrylate Derivatives:
Octocrylene, marketed in particular under the trademark "UVINUL N539" by BASF;
Etocrylene, marketed in particular under the trademark "UVINUL N35" by BASF;
Benzophenone Derivatives:
Benzophenone-1, marketed under the trademark "UVINUL 400" by BASF;
Benzophenone-2, marketed under the trademark "UVINUL D50" by BASF;
Benzophenone-3 or Oxybenzone, marketed under the trademark "UVINUL M40" by BASF;
Benzophenone-4, marketed under the trademark "UVINUL MS40" by BASF;
Benzophenone-5;
Benzophenone-6, marketed under the trademark "Helisorb 11" by Norquay;
Benzophenone-8, marketed under the trademark "Spectra-Sorb UV-24" by American Cyanamid;
Benzophenone-9, marketed under the trademark "UVINUL DS-49" by BASF;
Benzophenone-12;
n-Hexyl 2-(4-diethylamino-2-hydroxybenzoyl)benzoate, marketed under the trademark "UVINUL A+" by BASF;
Benzylidene Camphor Derivatives:
3-benzylidene camphor made under the trademark "MEXO-RYL SD" by CHIMEX;
4-methyl benzylidene camphor, marketed under the trademark "EUSOLEX 6300" by MERCK;
Benzylidene Camphor Sulfonic Acid, made under the trademark "MEXORYL SL" by CHIMEX;
Camphor Benzalkonium Methosulfate, made under the trademark "MEXORYL SO" by CHIMEX;
Terephthalylidene Dicamphor Sulfonic Acid, made under the trademark "MEXORYL SX" by CHIMEX;
Polyacrylamidomethyl Benzylidene Camphor, made under the trademark "MEXORYL SW" by CHIMEX;
Phenyl Benzimidazole Derivatives:
Phenylbenzimidazole Sulfonic Acid, marketed under the trademark "EUSOLEX 232" by MERCK;
Disodium Phenyl Dibenzimidazole Tetra-sulfonate, marketed under the trademark "NEO HELIOPAN AP" by HMRMANN and REIMER;
Phenyl Benzotriazole Derivatives:
Drometrizole Trisiloxane, marketed under the trademark "Silatrizole" by RHODIA CHIMIE;
Methylene bis-Benzotriazolyl Tetramethylbutylphenol, marketed in the solid form under the trademark "MIXXIM BB/100" by FAIRMOUNT CHEMICAL or in the micronized form in aqueous dispersion under the trademark "TINOSORB M" by CIBA SPECIALTY CHEMICALS;
Triazine Derivatives:
Bis-Ethylhexyloxyphenol Methoxyphenyl Triazine, marketed under the trademark "TINOSORBS" by CIBA GEIGY;
Ethylhexyl triazone, marketed under the trademark "UVINUL T150" by BASF;
Diethylhexyl Butamido Triazone, marketed under the trademark "UVASORB HEB" by SIGMA 3V;
2,4,6-Tris(dineopentyl 4'-aminobenzalmalonate)-s-triazine;
2,4,6-Tris-(diisobutyl 4'-aminobenzalmalonate)-s-triazine.
Anthranilic Derivatives:
Menthyl anthranilate, marketed under the trademark "NEO HELIOPAN MA" by HMRMANN and REIMER;
Imidazoline Derivatives:
Ethylhexyl Dimethoxybenzylidene Dioxoimidazoline Propionate;
Benzalmalonate Derivatives:
Di-neopentyl 4'-methoxybenzalmalonate;
Polyorganosiloxane with benzalmalonate functions, such as Polysilicone-15, marketed under the trademark "PARSOL SLX" by HOFFMANN LA ROCHE;
4,4-Diarylbutadiene derivatives:
1,1-Dicarboxy (2,2'-dimethylpropyl)-4,4-diphenylbutadiene;
Benzoxazole Derivatives:
2,4-Bis-[5-1 (dimethylpropyl)benzoxazol-2-yl-(4-phenyl)-imino]-6-(2-ethylhexyl)-imino-1,3,5-triazine, marketed under the trademark "Uvasorb K2A" by Sigma 3V;
and mixtures thereof.

Preferred complementary organic photoprotective agents are selected from among:
Ethylhexyl Methoxycinnamate;
Homosalate;
Ethylhexyl Salicylate;
Octocrylene;
Phenylbenzimidazole Sulfonic Acid;
Benzophenone-3;
Benzophenone-4;

Benzophenone-5;
n-Hexyl 2-(4-diethylamino-2-hydroxybenzoyl)-benzoate;
4-Methylbenzylidene camphor;
Terephthalylidene Dicamphor Sulfonic Acid;
Disodium Phenyl Dibenzimidazole Tetra-sulfonate;
Methylene bis-Benzotriazolyl Tetramethylbutylphenol;
Ethylhexyl triazone;
Bis-Ethylhexyloxyphenol Methoxyphenyl Triazine
Diethylhexyl Butamido Triazone;
2,4,6-Tris(dineopentyl 4'-aminobenzalmalonate)-s-triazine;
2,4,6-Tris-(diisobutyl 4'-aminobenzalmalonate)-s-triazine;
Drometrizole Trisiloxane;
Drometrizole Trisiloxane;
Polysilicone-15;
Di-neopentyl 4'-methoxybenzalmalonate;
1,1-Dicarboxy (2,2'-dimethylpropyl)-4,4-diphenylbutadiene;
2,4-Bis-[5-1 (dimethylpropyl)benzoxazol-2-yl-(4-phenyl)-imino]-6-(2-ethylhexyl)-imino-1,3,5-triazine;
and mixtures thereof.

Inorganic photoprotective agents are selected from pigments or nanopigments (mean primary particle size: generally from 5 nm to 100 nm, preferably from 10 nm to 50 nm) of metallic oxides which may or may not be coated, for example titanium oxide nanopigments (amorphous or crystalline in the rutile and/or anatase form), iron, zinc, zirconium or cerium, and mixtures thereof. Conventional coating agents include alumina and/or aluminum stearate. Such metallic oxide nanopigments, which may or may not be coated, are in particular described in EP-A-0,518,772 and EP-A-0,518,773.

The additional photoprotective agents are generally present in the compositions according to the invention in proportions of 0.01% to 20% by weight with respect to the total composition weight, preferably 0.1% to 10% by weight with respect to the total composition weight.

The compositions of the invention may be in any of the forms which are suitable for topical application, in particular in the form of aqueous gels, in the form of emulsions obtained by dispersion of a fat phase (also termed the oily phase) in an aqueous phase (O/W) or the reverse (W/H), or multiple emulsions (for example W/O/W or O/W/O or O/O/W). They may be more or less fluid and have the appearance of a white or colored cream, a pomade, a milk, a lotion, a serum, a paste, a powder, a solid stick, and may optionally be packaged as an aerosol and in the form of a foam or spray. These compositions are prepared using the usual methods.

In a particular embodiment of the invention, the composition is in the form of an emulsion and then comprises at least one oily phase. The proportion of the oily phase of the emulsion may be from 1% to 80% by weight, preferably 2% to 50% by weight and more preferably 2% to 40% by weight with respect to the total composition weight. The fats in the oily phase, in particular oils, and the emulsifying and co-emulsifying agents which may be present, used in the composition in the form of an emulsion are selected from those conventionally used in the cosmetics or dermatological field. The emulsifying and co-emulsifying agent, when present, are generally present in a proportion of 0.1% to 30% by weight, preferably 0.3% to 20% by weight and more preferably 0.5% to 15% by weight with respect to the total composition weight. The emulsion may also contain lipid vesicles in addition to or in place of the emulsifying and/or co-emulsifying agents.

The emulsions generally contain at least one emulsifying agent selected from amphoteric, anionic, cationic or nonionic emulsifying agents used alone or as a mixture. The emulsifying agents are suitably selected as a function of the continuous phase of the emulsion to be produced (W/H or O/w). When the emulsion is a multiple emulsion, it generally comprises an emulsifying agent in the primary emulsion and an emulsifying agent in the external phase into which the primary emulsion is introduced.

Emulsifying agents which may be used to prepare W/H emulsions which may be cited, are for example alkyl esters or sorbitan ethers, glycerol or sugars; silicone surfactants such as dimethicone copolyols, such as the mixture of cyclomethicone and dimethicone copolyol, marketed under the trademarks DC 5225 C and DC 3225 C by Dow Corning and such as alkyl-dimethicone copolyols such as Laurylmethicone copolyol marketed under the trademark "Dow Corning 5200 Formulation Aid" by Dow Corning, Cetyl dimethicone copolyol marketed under the trademark Abil EM 90® by Goldschmidt and the mixture of Polyglyceryl-4 isostearate/Cetyl dimethicone copolyol/Hexyl laurate marketed under the trademark Abil WE 09® by Goldschmidt. It is also possible to add thereto one or more co-emulsifying agents which, advantageously, may be selected from the group comprising esters of fatty acids with a branched chain and polyol, in particular esters of fatty acid with a branched chain and glycerol and/or sorbitan and, for example, polyglyceryl isostearate, such as the product marketed under the trademark Isolan GI 34 by Goldschmidt, sorbitan isostearate, such as the product marketed under the trademark Arlacel 987 by ICI, sorbitan isostearate and glycerol, such as the product marketed under the trademark Arlacel 986 by ICI, and mixtures thereof.

Examples of emulsifying agents suitable for the preparation of O/W emulsions which may be cited are nonionic emulsifying agents such as esters of fatty acids and oxyalkylenated polyols (more particularly polyoxyethylenated), for example polyethylene glycol stearates such as PEG-100 stearate, PEG-50 stearate and PEG-40 stearate; esters of fatty acids and oxyalkylenated sorbitan comprising 20 to 100 OE, for example, and for example those marketed under the trademark Tween 20 or Tween 60 by Uniqema; ethers of oxyalkylenated (oxyethylenated and/or oxypropylenated) fatty alcohols; esters of sugars, alkoxylated or not, such as sucrose stearate and such as PEG-20 methylglucose sesquistearate; sorbitan esters such as sorbitan palmitate marketed under the trademark Span 40 by Uniqema; esters of a dibasic acid and a fatty alcohol, such as dimyristyl tartrate; mixtures of these emulsifying agents such as a mixture of glyceryl stearate and PEG-100 stearate (CTFA name: Glyceryl Stearate/PEG-100 Stearate) marketed under the trademark Arlacel 165 by Uniqema and under the trademark SIMULSOL 165 by SEPPIC; or the mixture of dimyristyl tartrate, cetearyl alcohol, Pareth-7 and PEG-25 laureth-25, marketed under the trademark Cosmacol PSE by Sasol (CTFA name: Dimyristyl tartrate/cetearyl alcohol/12-15 Pareth 7/PPG 25 laureth 25); mixtures of fatty alcohols and alkylglycoside, such as the cetearyl alcohol/cetearyl glucoside mixture, for example the commercially available product marketed under the trademark MONTANOV 68 by SEPPIC.

Co-emulsifying agents may be added to said emulsifying agents, such as fatty alcohols containing 8 to 26 carbon atoms, such as cetyl alcohol, stearyl alcohol and a mixture thereof (cetearyl alcohol), octyldodecanol, 2-butyloctanol, 2-hexyldecanol, 2-undecylpentadecanol or oleic alcohol, or fatty acids, for example.

It is also possible to prepare emulsions without emulsifying surfactants or containing less than 0.5% of the total composition weight, using suitable compounds which can stabilize said emulsions, for example amphiphilic polymers, electrolytes.

When the composition of the invention is in the form of an emulsion, it comprises at least one oily phase which contains at least one oil, in particular a cosmetic oil. The term "oil" means a fat which is liquid at ambient temperature (25° C.).

Examples of oils which can be used in the compositions of the invention are hydrocarbon-containing oils of animal origin such as perhydrosqualene (or squalane); hydrocarbon-containing oils of vegetable origin, such as caprylic/capric acid triglycerides such as those marketed by Stearineries Dubois or those marketed under the trademark Miglyol 810, 812 and 818 by Dynamit Nobel, or oils of vegetable origin, for example sunflower, corn, soya, gourd, grapeseed, sesame, hazelnut, apricot, macadamia nut, arara, coriander, castor, avocado, jojoba oil, shea butter oil; synthesized oils; silicone oils such as volatile or non-volatile polymethylsiloxanes (PDMS) with a linear or cyclic silicone chain, which are liquid or pasty at ambient temperature; fluorinated oils such as partially hydrocarbonated and/or silicone oils, such as those described in JP-A-2-295912; ethers such as dicapryl ether (CTFA name: Dicaprylyl ether); and benzoates of $C_{12}$-$C_{15}$ fatty alcohols (Finsolv TN from FINETEX); arylalkyl benzoate derivatives such as 2-phenylethyl benzoate (X-Tend 226 from ISP); amide oils such as isopropyl N-lauroylsarcosinate (ELDEW SL-205 from Ajimoto) and mixtures thereof.

The oily phase may also comprise one or more fats selected, for example, from fatty alcohols (cetyl alcohol, stearyl alcohol, cetearyl alcohol), fatty acids (stearic acid) and waxes (paraffin, polyethylene waxes, carnauba, beeswax).

The compositions of the invention may also contain one or more organic solvents which may be selected from the group constituted by hydrophilic organic solvents, lipophilic organic solvents, amphiphilic solvents or mixtures thereof.

Examples of hydrophilic organic solvents which are representative, for example, are linear or branched monohydric alcohols containing 1 to 8 carbon atoms, such as ethanol, propanol, butanol, isopropanol or isobutanol; polyethylene glycols containing 6 to 80 ethylene oxides; polyols such as propylene glycol, isoprene glycol, butylene glycol, glycerol or sorbitol; mono- or di-alkyl isosorbides the alkyl groups of which contain 1 to 5 carbon atoms, such as dimethyl isosorbide; glycol ethers such as diethylene glycol mono-methyl or mono-ethyl ether and propylene glycol ethers such as dipropylene glycol methyl ether.

Amphiphilic organic solvents which are exemplary include polypropylene glycol (PPG) derivatives, such as esters of polypropylene glycol and fatty acids, PPG and fatty alcohol such as PPG-23 oleyl ether and PPG-36 oleate.

Examples of lipophilic organic solvents which are exemplary are fatty esters such as diisopropyl adipate, dioctyl adipate or alkyl benzoates.

The compositions of the present invention may also comprise conventional cosmetic adjuvants selected from softeners, moisturizers, opacifying agents, stabilizers, emollients, silicones, anti-foaming agents, fragrances, preservatives, anionic, cationic, nonionic, zwitterionic or amphoteric surfactants, fillers, polymers, propellants, alkalinizing or acidifying agents or any other ingredient which is normally used in the cosmetics and/or dermatological field.

Hydrophilic thickeners which are exemplary include carboxyvinyl polymers such as carbopols (carbomers) and Pemulens (Copolymer acrylate/C10-C30-alkylacrylate); cellulose derivatives such as hydroxyethylcellulose; polysaccharides and in particular, gums such as xanthan gum; and mixtures thereof.

Lipophilic thickeners which are exemplary include modified clays, such as hectorite and its derivatives, for example products marketed under the trademark Bentone.

Preservatives which are exemplary include parahydroxybenzoic acid esters also known as Parabens® (in particular methyl paraben, ethyl paraben, propyl paraben), phenoxyethanol, formol liberators such as, for example, imidazolidinyl urea or diazolidinyl urea, chlorhexidine digluconate, sodium benzoate, caprylyl glycol, iodopropynyl butyl carbamate, pentylene glycol, alkyl trimethylammonium bromide such as myristyl-trimethylammonium bromide (CTFA name: Myrtrimonium bromide), dodecyl-trimethylammonium bromide, hexadecyl-trimethylammonium bromide, and mixtures thereof such as the mixture marketed under the trademark Cetrimide® by FEF CHEMICALS. The preservative may be present in the composition of the invention in an amount of 0.001% to 10% by weight with respect to the total composition weight, especially 0.1% to 5% by weight, and in particular 0.2% to 3% by weight.

Examples of fillers which may be included in the compositions of the invention are, for example, pigments; silica powder; talc; polyamide particles, in particular those marketed under the trademark ORGASOL by Atochem; polyethylene powders; powders of natural organic materials such as starch powders, in particular of corn, wheat or rice starch, which may or may not be cross-linked, such as powders of starch cross-linked by octenylsuccinate anhydride, marketed under the trademark DRY-FLO by National Starch; microspheres based on acrylic copolymers, such as those formed from an ethylene glycol dimethacrylate/lauryl methacrylate copolymer marketed by Dow Corning under the trademark POLYTRAP; polymethylmethacrylate powders such as those marketed under the trademark MICROPEARL M 100 by Matsumoto; expanded powders such as hollow microspheres, in particular microspheres marketed under the trademark EXPANCEL by Kemanord Plast or under the trademark MICROPEARL F 80 ED by Matsumoto; silicone resin microbeads, such as those marketed under the trademark TOSPEARL by Toshiba Silicone; polyurethane powders, such as hexamethylene diisocyanate/trimethylol hexyllactone copolymer marketed under the trademark Plastic Powder D-400 by Toshiba Pigment (CTFA name: HDI/Trimethylol Hexyllactone Crosspolymer); and mixtures thereof. When they are present, these fillers may be in quantities of 0.001% to 20% by weight, preferably 0.1% to 10% by weight and more preferably 1% to 5% by weight with respect to the total composition weight.

Clearly, one skilled in the art will take care to select any complementary compounds as cited above and/or their quantities such that the advantageous properties intrinsically attached to the combination in accordance with the invention are not impaired or not substantially impaired by the envisaged adjuncts.

The compositions of the invention may constitute a skin care product, in particular for the face, the neck, the contours of the eye, the body; or a skin makeup product such as a tinting product (in particular a foundation), an eye shadow, a blusher, an eye-liner, a concealer, a body makeup product, a sun protection product or a skin cleansing product. Preferably, the composition of the invention is a sun protection product.

The composition is generally not washed off, but may be washed off if it constitutes a cleansing product, in particular a foaming product.

The present invention also provides a regime or regimen for the cosmetic treatment of a keratinous material such as the skin, eyelashes, eyebrows, nails or mucosal membranes, wherein a composition as defined above is topically applied onto the keratinous material.

The compositions of the invention may be in the form of sprayable fluid lotions in accordance with the invention which are applied to the skin or the hair in the form of fine particles using pressurization devices. The devices of the invention are well known to one skilled in the art and include non-aerosol pumps or atomizers, aerosol receptacles comprising a propellant and aerosol pumps using compressed air as the propellant. These latter have been described in U.S. Pat. Nos. 4,077,441 and 4,850,517.

Compositions packaged in aerosol form in accordance with the invention generally contain conventional propellants such as hydrofluorinated compounds, dichlorodifluoromethane, difluoroethane, dimethylether, isobutane, n-butane, propane or trichlorofluoromethane. They are preferably present in quantities of 15% to 50% by weight with respect to the total composition weight.

In order to further illustrate the present invention and the advantages thereof, the following specific examples are given, it being understood that same are intended only as illustrative and in nowise limitative. In said examples to follow, all parts and percentages are given by weight, unless otherwise indicated.

SYNTHESIS EXAMPLES

Example 1

Preparation of Compound (k) with Formula (6)

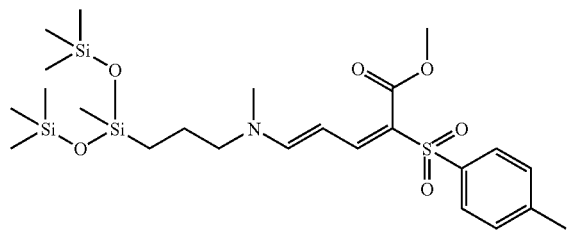

(k)

First step: Preparation of methyl 5-[allyl(methyl) amino]-2-[(4-methylphenyl)sulfonyl]penta-2,4-dienoate 3-Anilinoacrolein aniline (1.2 g, $5.4 \times 10^{-3}$ mol) and methyl para-toluene sulfonyl acetate (1.48 g, $6.48 \times 10^{-3}$ mol) was heated to 85-90° C. in 5 ml of acetic anhydride for 2 hours 30 minutes. The acetic anhydride was evaporated to dryness under reduced pressure. The oil obtained was taken up in 5 ml of ethanol. N-Methyl allylamine (1.115 ml, 0.0117 mol) was added and the mixture was heated under reflux for 4 hours 30 minutes. The ethanol was evaporated to dryness under reduced pressure. The orange-brown oil obtained was purified on a silica chromatographic column (eluent: EtOAc/ heptane 20:80, then gradient to 30:70). 1.48 g of fractions (yield: 77%) of methyl 5-[allyl(methyl)amino]-2-[(4-methylphenyl)sulponyl]penta-2,4-dienoate were obtained in the form of a pale yellow oil:

| UV (CH$_2$Cl$_2$): | $\lambda_{max}$ = 370 nm | $E_{1\%}$ = 1346 |
| | $\lambda_{max}$ = 356 nm (shoulder) | $E_{1\%}$ = 1031 |

Second step: Preparation of compound of Example 1

0.371 g ($1.67 \times 10^{-3}$ mol) of heptamethyl-trisiloxane was added dropwise over 10 minutes to a solution of the preceding product (0.508 g, $1.51 \times 10^{-3}$ mol) and catalyst (complex containing 3-3.5% by weight of Pt in cyclovinylmethylsiloxane, from Hüls Petrarch PC085: 100 µl) in 2 ml of dry toluene heated to 80° C. It was left at this temperature for 6 hours. The reaction mixture was concentrated. It was taken up in dichloromethane and this solution was passed over a bed of Celite. The pale yellow oil obtained was chromatographed on a silica column (eluent: heptane/EtOAc 65:35). 0.45 g (yield: 53%) of fractions of the derivative of Example 1 was obtained in the form of a pale yellow oil which crystallized slowly:

UV (Ethanol):

| $\lambda_{max}$ = 372 nm | $E_{1\%}$ = 1154 |
| $\lambda_{max}$ = 356 nm (shoulder) | $E_{1\%}$ = 773 |

Example 2

Preparation of Compound (f) with Formula (4)

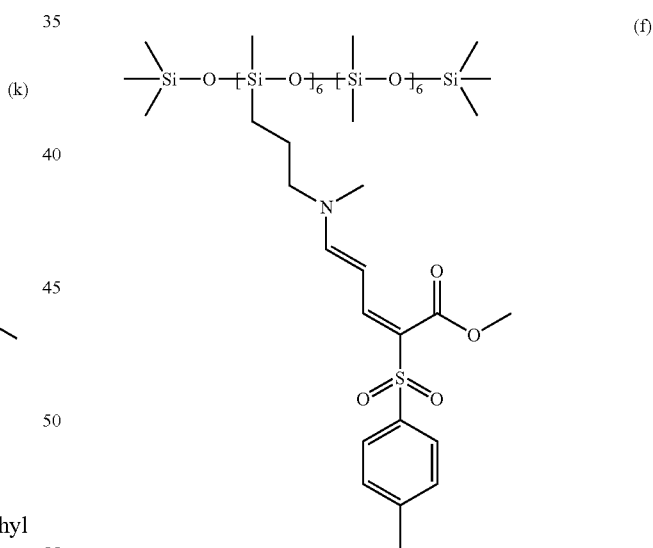

(f)

0.325 g (2 meq SiH) of methylhydro (50-55%) dimethylsiloxane (45-50%) copolymer (PS122.5 from Petrarch) was added dropwise over 10 minutes to a solution of methyl 5-[allyl(methyl)amino]-2-[(4-methylphenyl)sulfonyl]penta-2,4-dienoate (0.7 g, $2.1 \times 10^{-3}$ mol) obtained in the first step of Example 1 and catalyst (complex containing 3-3.5% by weight of Pt in cyclovinylmethylsiloxane, from Hüls Petrarch PC085: 80 µl) in 2 ml of dry toluene heated to 80° C. It was left at this temperature for 6 hours. The reaction mixture was concentrated. It was taken up in dichloromethane and this solution was passed over a bed of Celite. The pale yellow oil obtained was chromatographed on a silica column (eluent: $CH_2Cl_2$). 0.92 g of fractions of the derivative of Example 2 was thus obtained in the form of a viscous pale yellow oil:

UV (Ethanol)

$\lambda_{max}=371$ nm $E_{1\%}=728$

Example 3

Preparation of a Mixture of Compounds (m) with Formula (6)

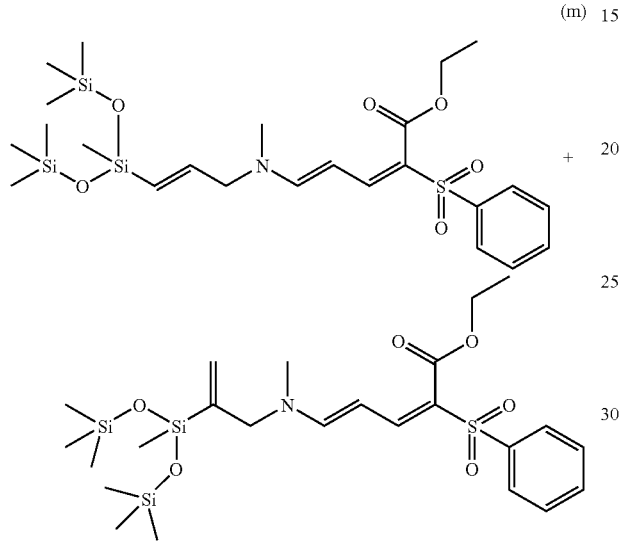

(m)

First step: Preparation of ethyl 5-[methyl(prop-2-ynyl)amino]-2-(phenylsulfonyl)penta-2,4-dienoate 3-Anilinoacrolein aniline (1.5 g, $6.75\times10^{-3}$ mol) and ethyl phenylsulfonyl acetate (1.848 g, $8.1\times10^{-3}$ mol) was heated to 85-90° C. in 5 ml of acetic anhydride for 3 hours. The acetic anhydride was evaporated to dryness under reduced pressure. The oil obtained was taken up in 5 ml of ethanol. N-Methyl propargylamine (1.22 ml, 0.0146 mol) was added and the mixture was heated under reflux for 5 hours. The ethanol was evaporated to dryness under reduced pressure. The orangish oil obtained was purified on a silica chromatographic column (eluent: EtOAc/heptane 50:50, then gradient to 30:70). 1.68 g of fractions (yield: 71%) of ethyl 5-[methyl(prop-2-ynyl)amino]-2-(phenylsulfonyl)penta-2,4-dienoate were obtained in the form of a pale yellow oil:

| UV ($CH_2Cl_2$): | $\lambda_{max} = 366$ nm | $E_{1\%} = 1367$ |
|---|---|---|
| | $\lambda_{max} = 358$ nm (shoulder) | $E_{1\%} = 1298$ |

Second step: Preparation of compound of Example 3

0.413 g ($1.86\times10^{-3}$ mol) of heptamethyltrisiloxane was added dropwise over 10 minutes to a solution of the preceding product (0.562 g, $1.69\times10^{-3}$ mol) and catalyst (complex containing 3-3.5% by weight of Pt in cyclovinylmethylsiloxane, from Hüls Petrarch PC085: 60 µl) in 2 ml of dry toluene heated to 80° C. It was left at this temperature for 6 hours. The reaction mixture was concentrated. It was taken up in dichloromethane and this solution was passed over a bed of Celite. The pale yellow oil obtained was chromatographed on a silica column (eluent: $CH_2Cl_2$). 0.35 g (yield: 37%) of fractions of the derivative of Example 3 was obtained in the form of a pale orangish yellow oil which crystallized slowly in a ratio of 25:75 as determined by $^1$H NMR:

UV (Ethanol):

| $\lambda_{max} = 366$ nm | $E_{1\%} = 1058$ |
|---|---|
| $\lambda_{max} = 356$ nm (shoulder) | $E_{1\%} = 705$ |

Example 4

Preparation of Compound (n) with Formula (6)

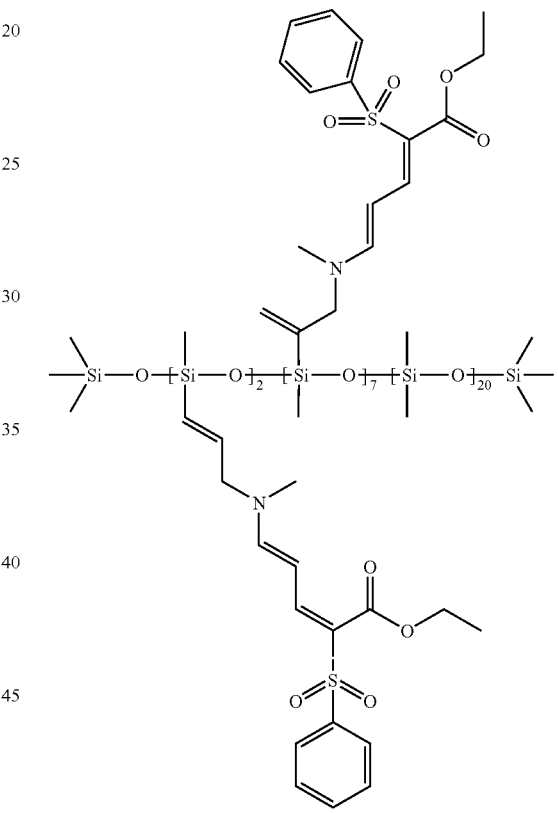

1.24 g (2.3 meq SiH) of methylhydro (30-35%) dimethylsiloxane (65-70%) copolymer (PDMS oil with SiH 628V14 from Rhône Poulenc) were added dropwise over 10 minutes to a solution of ethyl 5-[methyl(prop-2-ynyl)amino]-2-(phenylsulfonyl)penta-2,4-dienoate (0.8 g, $2.41\times10^{-3}$ mol) obtained in the first step of Example 3 and catalyst (complex containing 3-3.5% by weight of Pt in cyclovinylmethylsiloxane, from Hüls Petrarch PC085: 110 µl) in 2 ml of dry toluene heated to 80° C. It was left at this temperature for 6 hours. The reaction mixture was concentrated. It was taken up in dichloromethane and this solution was passed over a bed of Celite. The pale yellow oil obtained was chromatographed on a silica column (eluent: $CH_2Cl_2$). 1.82 g of fractions of the derivative of Example 4 were obtained in the form of a viscous pale yellow oil:

UV (Ethanol):

$\lambda_{max}=366$ nm $E_{1\%}=270$

Example 5

Preparation of Compound (p) with Formula (6)

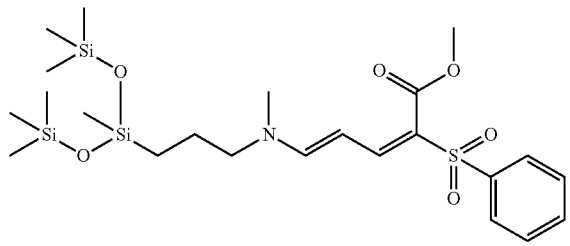

First step: Preparation of methyl 5-[allyl-(methyl)amino]-2-(phenylsulfonyl)penta-2,4-dienoate 3-Anilinoacrolein aniline (9.2 g, 0.0414 mol) and methyl sulfonyl acetate (10.6 g, 0.0497 mol) were heated to 50° C. in 50 ml of acetic anhydride for 1 hour. The acetic anhydride was evaporated to dryness under reduced pressure. The oil obtained was taken up in 50 ml of ethanol. N-Methyl allylamine (12 ml, 0.126 mol) was added and the mixture was heated under reflux for 1 hour 15 minutes. The ethanol was evaporated to dryness under reduced pressure. The brown solid obtained was purified by passage over a silica chromatographic column (eluent: EtOAc/heptane 40:60, then gradient to 50:50). 10 g of fractions (yield: 77%) of methyl 5-[allyl (methyl)amino]-2-(phenylsulfonyl)penta-2,4-dienoate were obtained in the form of a yellow solid and used as is in the next step:

Second step: Preparation of compound of Example 1

7.1 g (0.0305 mol) of heptamethyltrisiloxane were added dropwise over 10 minutes to a solution of the preceding product (9.3 g, 0.029 mol) and catalyst (complex containing 3-3.5% by weight of Pt in cyclovinylmethylsiloxane, from Hüls Petrarch PC085: 250 µl) in 55 ml of dry toluene heated to 60° C. The reaction mixture was heated under reflux for 3 hours. The reaction mixture was concentrated. The crude solid obtained was re-crystallized from heptane then chromatographed on a silica column (eluent: heptane/EtOAc 70:30). 8.6 g (yield: 55%) of fractions of the derivative of Example 5 were obtained in the form of a pale yellow powder: m.p. 118-119° C.
UV (Ethanol):

$\lambda_{max}$=371 nm $E_{1\%}$=1370

Photostability Tests of Dibenzoylmethane Sunscreen:
The following two emulsions A and B were produced:
Formula A (Invention):

| | |
|---|---|
| Cetearyl glucoside/cetearyl alcohol mixture (MONTANOV 68) | 7.5 g |
| Benzoate of $C_{12}/C_{15}$ alcohols (WITCONOL TN-WITCO) | 20 g |
| Compound k) | 4 g |
| 4-tert-Butyl-4'-methoxy dibenzoylmethane | 1 g |
| Glycerin | 5 g |
| Preservatives | qs |
| Demineralized water | qs 100 g |

Formula B (Outside Invention):

| | |
|---|---|
| Cetearyl glucoside/cetearyl alcohol mixture (MONTANOV 68) | 7.5 g |
| Benzoate of C12/C15 alcohols (WITCONOL TN-WITCO) | 20 g |
| 4-tert-Butyl-4'-methoxy dibenzoylmethane | 1 g |
| Glycerin | 5 g |
| Preservatives | qs |
| Demineralized water | qs 100 g |

About 20 mg of the above emulsion were spread over 10 $cm^2$ of the surface of a ground silica disc: the exact quantity of the deposit was determined by weighing.

The films of the solutions were irradiated for one hour using an ORIEL solar simulator (UV-A=14.4 $mW/cm^2$; UV-B=0.43 $mW/cm^2$) in a dose of 12 $J/cm^2$, then extracted with 10 ml of ethanol with 10% isopropanol and 5 min of ultrasound. The products were quantified by HPLC carried out on the extracts.

The degree of loss was determined by comparing the quantities of product present in the irradiated samples and, in the simultaneously prepared non-irradiated references treated in the same manner (mean of 3 samples).

Photostability Results:

| Test composition | % disappearance of Parsol 1789 (mean loss) |
|---|---|
| Formula A (Parsol 1789 + compound k) | 5 ± 1.7 |
| Formula B (Parsol 1789 alone) | 45 ± 2.4 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable photostabilized cosmetic/dermatological composition comprising at least one dibenzoylmethane compound UV-A screening agent and at least one merocyanine sulfone compound of formula (1), formulated into a topically applicable, cosmetically/dermatologically acceptable support therefor:

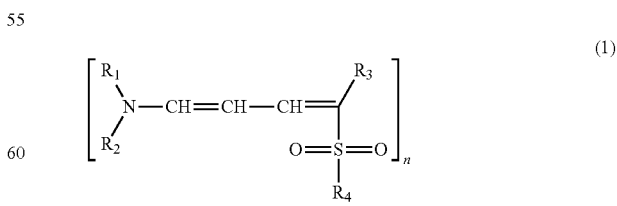

in which:

$R_1$ and $R_2$, which may be identical or different, are each H, a $C_1$-$C_{22}$ alkyl radical, a $C_3$-$C_8$ cycloalkyl radical, a $C_6$-$C_{20}$ aryl radical, with the proviso that only one of $R_1$, $R_2$ is H and that $R_1$ and $R_2$ may together form, with the nitrogen from which they depend, a cycle containing the —$(CH_2)_m$— group, which may be uninterrupted or interrupted by —O— or by —NH—;

$R_3$ is a carboxyl group, —$COOR_4$, —$CONHR_4$, —$COR_4$, —$CONR_1R_4$, —CN or —$SO_2R_4$;

the radicals $R_4$, which may be identical or different, are each a $C_1$-$C_{22}$ alkyl Radical, a $C_3$-$C_8$ cycloalkyl radical or a $C_6$-$C_{20}$ aryl radical;

m is 1-7:

n is 1-4;

with the provisos that:
(i) when n=2, $R_1$, $R_4$ is an alkyl di-radical or $R_1$ and $R_2$ together form with 2 nitrogen atoms, a divalent —$(CH_2)_m$— radical;
(ii) when n=3, $R_1$ and $R_4$ are a trivalent radical;
(iii) when n=4, $R_1$, $R_4$ are a tetravalent radical; and
(iv) $R_1$ and $R_2$ are not simultaneously a hydrogen atom.

2. The cosmetic/dermatological composition as defined by claim 1, in which said at least one dibenzoylmethane compound is selected from the group consisting of:
2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane; and
2,6-dimethyl-4-tert-butyl-4'-methoxydibenzoylmethane.

3. The cosmetic/dermatological composition as defined by claim 2, in which said at least one dibenzoylmethane compound comprises 4-(tert-butyl)4'-methoxydibenzoylmethane or Butyl Methoxy Dibenzoylmethane.

4. The cosmetic/dermatological composition as defined by claim 1, wherein the following conditions are satisfied:

$R_1$ and $R_2$, which may be identical or different, are each a $C_1$-$C_{12}$ alkyl radical;
$R_3$ is a $COOR_5$ group;
$R_4$ is a phenyl group;
$R_5$ is a $C_1$-$C_{12}$ alkyl radical; and
n equals 1 or 2.

5. The cosmetic/dermatological composition as defined by claim 4, in which said at least one merocyanine sulfone compound is selected from the group consisting of the following compounds:

Ethyl 5-(dihexylamino)-2-(phenylsulfony)-2,4-pentadienoate:

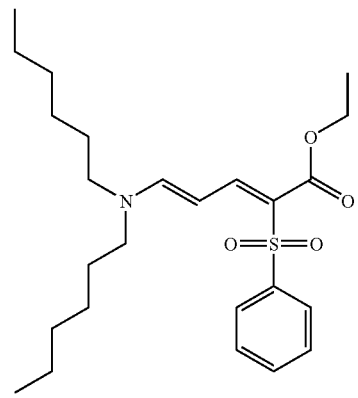

(a)

Octyl 5-N,N-diethylamino-2-phenylsulfonyl-2,4-pentadienoate:

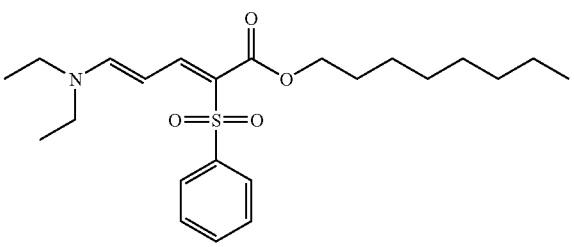

(b)

Lauryl 5-N,N-diethylamino-2-phenylsulfonyl-2,4-pentadienoate:

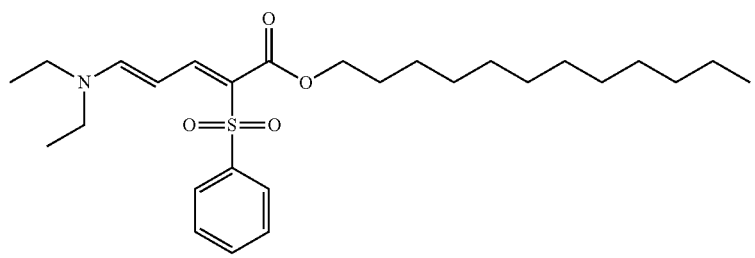

(c)

-continued

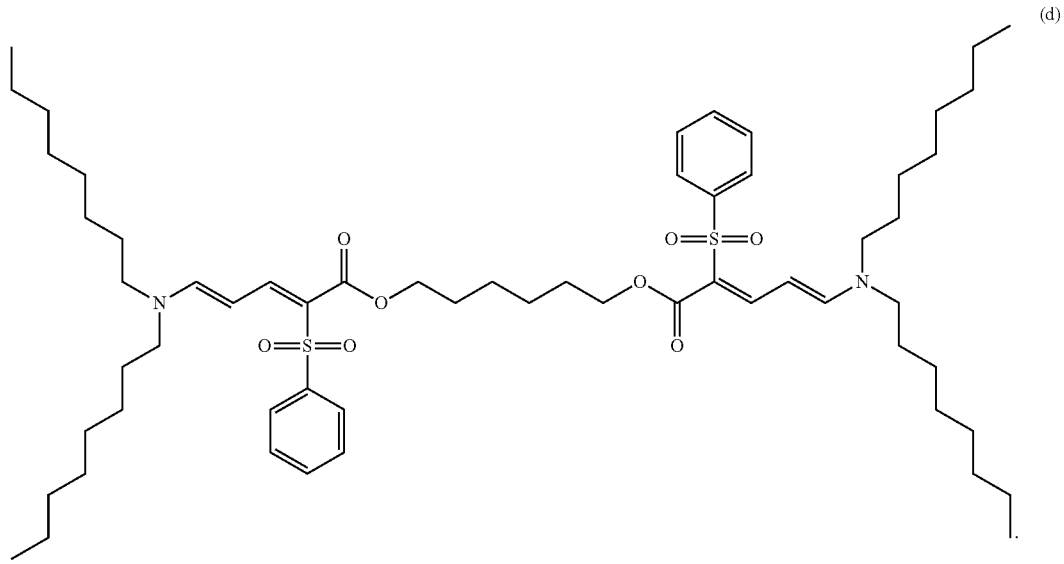
(d)

6. A topically applicable photostabilized cosmetic/dermatological composition comprising at least one dibenzoylmethane compound UV-A screening agent and at least one merocyanine sulfone compound, formulated into a topically applicable, cosmetically/dermatologically acceptable support therefor, in which said at least one merocyanine sulfone compound has one or another of the following formulae (4) and (6):

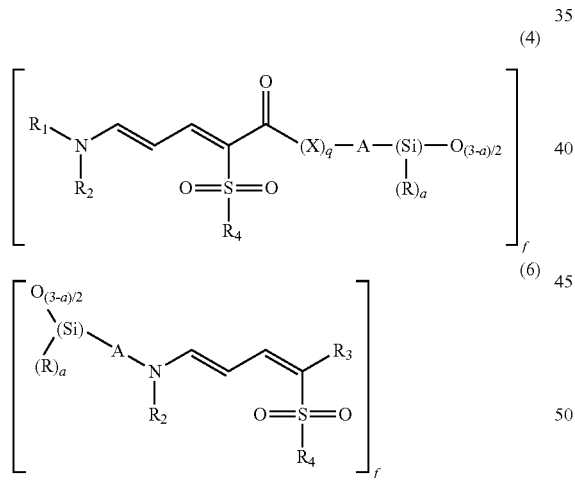

in which:

X is —O—, —NR$_5$—;

wherein

R$_1$ and R$_2$ which may be identical or different are each H a C$_1$-C$_{22}$ alkyl radical, a C$_3$-C$_8$ cycloalkyl radical, a C$_6$-C$_{20}$ aryl radical, with the proviso that only one of R$_1$, R$_2$ is H and that R$_1$ and R$_2$ may together form, with the nitrogen from which they depend, a cycle containing the —(CH$_2$)$_m$— group, which may be uninterrupted or interrupted by —O— or by —NH—;

R$_3$ is a carboxyl group, —COOR$_4$, —CONHR$_4$, —COR$_4$, —CONR$_1$R$_4$, —CN or —SO$_2$R$_4$;

the radicals R$_4$, which may be identical or different, are each a C$_1$-C$_{22}$ alkyl radical, a C$_3$-C$_8$ cycloalkyl radical or a C$_6$-C$_{20}$ aryl radical;

m is 1-7;

R$_5$ is a C$_1$-C$_5$ alkyl radical;

q=0 or 1;

Y is a divalent C$_1$-C$_5$ alkyl radical, optionally substituted with C$_1$-C$_4$ alkyl radicals and/or containing —O—, —S— atoms or with an —NR$_1$ group;

the radicals R, which may be identical or different, are each a linear or branched C$_1$-C$_{20}$ alkyl radical which may optionally be halogenated, a C$_6$-C$_{12}$ aryl radical or a C$_1$-C$_{10}$ alkoxy radical;

a=0 to 3;

A is a divalent radical selected from the group consisting of methylene, ethylene and a group having one of the following formulae (7), (8) or (9):

in which:

Z is a linear or branched, saturated or unsaturated C$_1$-C$_6$ alkylene radical, optionally substituted with a hydroxyl radical or a linear or branched, saturated or unsaturated C$_1$-C$_8$ alkyl radical;

W is a hydrogen atom; a hydroxyl radical or a linear or branched, saturated or unsaturated C$_1$-C$_8$ alkyl radical;

p is 0 or 1; and f=1 or 2.

7. The cosmetic/dermatological composition as defined by claim 6, in which the compound of formula (4) or (6) further comprises structural units of formula $(R)_b—(Si)(O)_{(4-b)/2}$ in which:

R is as defined in formulae (1) to (3);
b=1, 2 or 3.

8. The cosmetic/dermatological composition as defined by claim 7, in which the $—(Si)(R)_a(O)_{(3-a)/2}$ groups are set forth by the following formulae (10), (11) or (12):

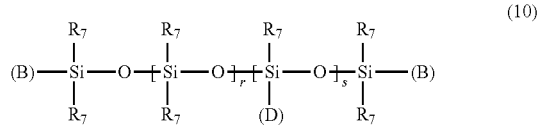

(10)

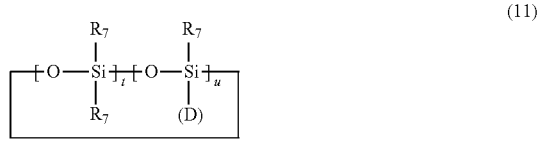

(11)

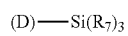

(12)

in which:

D binds the silicone chain of group A to chromophores having formulae (4) to (6);

the radicals $R_7$, which may be identical or different, are each selected from the group consisting of linear or branched $C_1$-$C_{30}$ alkyl, phenyl, 3,3,3-trifluoropropyl and trimethylsilyloxy radicals, at least 80% by number of radicals $R_7$ being methyl;

the radicals (B), which may be identical or different, are each selected from the group consisting of the radicals $R_8$ and radical A;

r is a whole number ranging from 0 to 200 inclusive, and s is a whole number ranging from 0 to 50 inclusive, and if s =0, at least one of the two symbols (B) designates A;

u is a whole number ranging from 1 to 10 inclusive, and t is a whole number ranging from 0 to 10 inclusive, with the proviso that t+u equals 3 or more.

9. The cosmetic/dermatological composition as defined by claim 8, in which said at least one merocyanine sulfone compound comprises a linear or cyclic diorganosiloxane of formula (10) or (11) having at least one of the following characteristics:

$R_7$ is methyl;
B is methyl.

10. The cosmetic/dermatological composition as defined by claim 6, in which said at least one compound of formula (4) is/are selected from the group consisting of the following compounds:

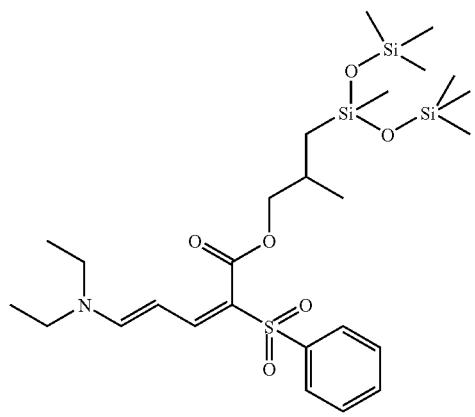

(e)

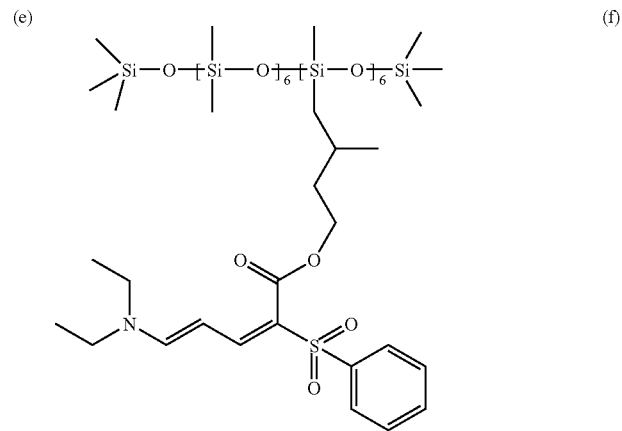

(f)

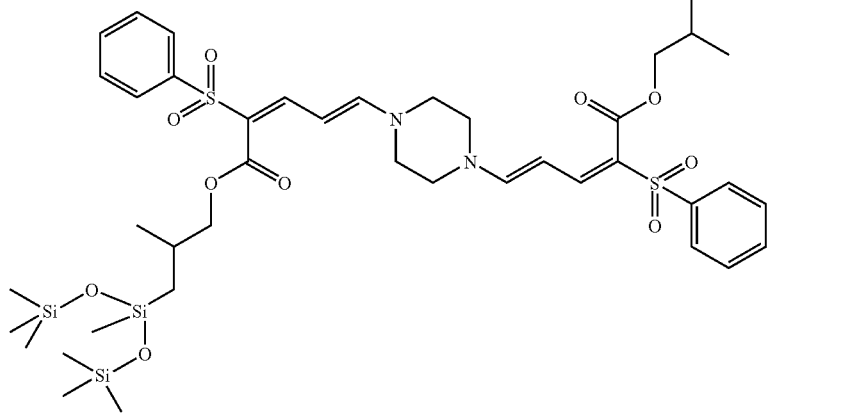

(g)

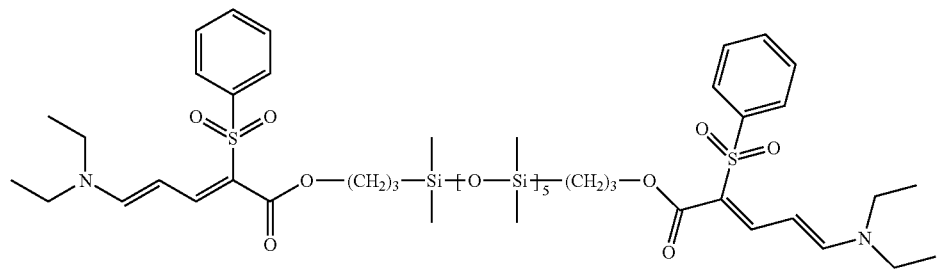
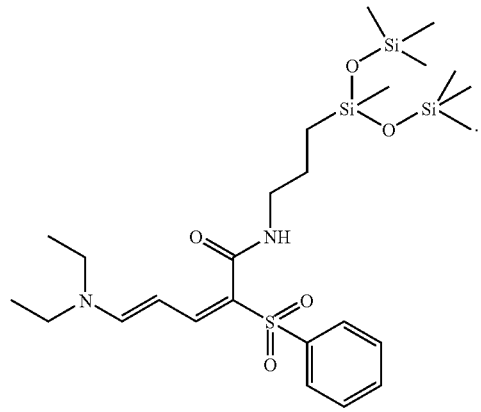
11. The cosmetic/dermatological composition as defined by claim 6, in which said at least one compound of formula (6) is/are selected from the group consisting of the following compounds:
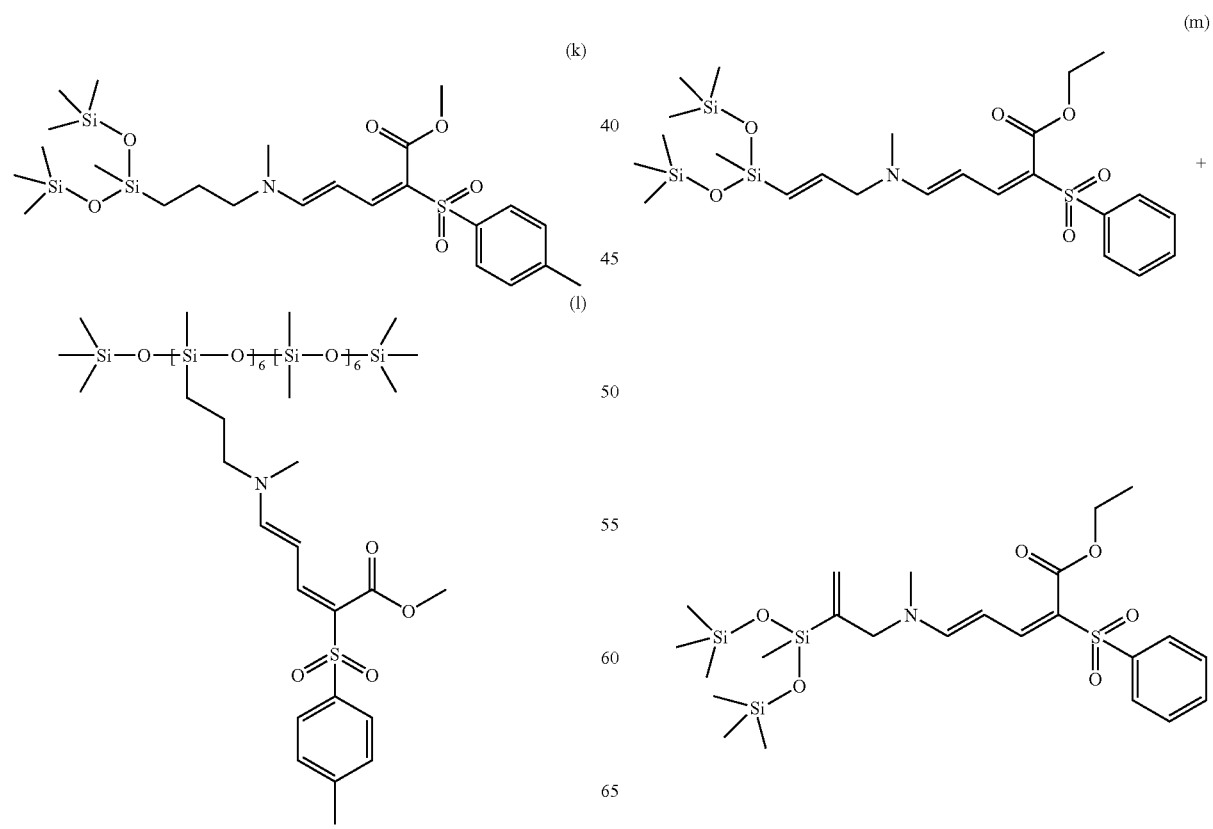

-continued

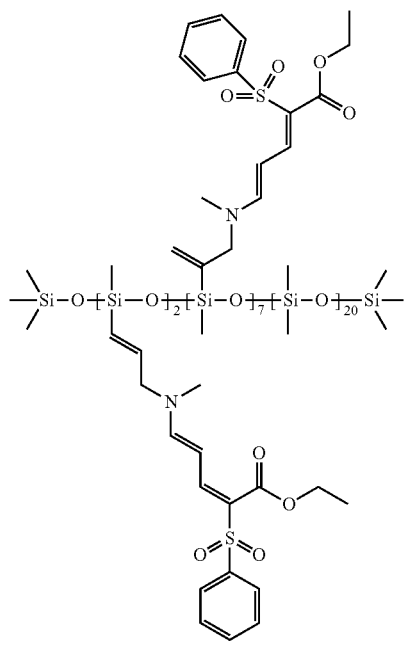

(n)

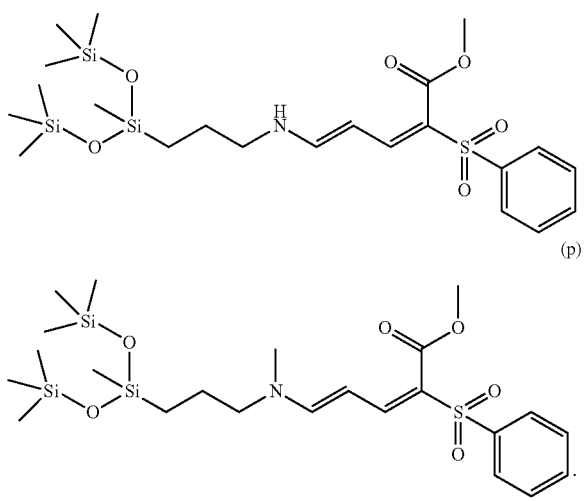

(o)

(p)

12. The cosmetic/dermatological composition as defined by claim 1, in which said at least one dibenzoylmethane compound is/are present in amounts of 0.01% to 20% by weight with respect to the total composition weight.

13. The cosmetic/dermatological composition as defined by claim 12, in which said at least one merocyanine sulfone compound is/are present in amounts of 0.01% to 20% by weight with respect to the total composition weight.

14. The cosmetic/dermatological composition as defined by claim 1, further comprising other organic or inorganic photoprotective agents that are active in the UV-A and/or UV-B range and that are water-soluble or liposoluble or insoluble in the conventional cosmetic solvents.

15. The cosmetic/dermatological composition as defined by claim 14, comprising additional organic photoprotective agents selected from the group consisting of anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis(benzoazolyl) derivatives; p-aminobenzoic acid (PABA) derivatives; methylene bis(hydroxyphenylbenzotriazole) derivatives; benzoxazole derivatives; screening polymers and screening silicones; α-alkylstyrene-derived dimers; 4,4-diarylbutadienes and mixtures thereof.

16. The cosmetic/dermatological composition as defined by claim 15, comprising additional organic UV screening agent(s) selected from the group consisting of the following compounds:
Ethylhexyl Methoxycinnamate;
Homosalate;
Ethylhexyl Salicylate;
Octocrylene;
Phenylbenzimidazole Sulfonic Acid;
Benzophenone-3;
Benzophenone-4;
Benzophenone-5;
n-Hexyl 2-(4-diethylamino-2-hydroxybenzoyl)benzoate;
4-Methylbenzylidene camphor;
Terephthalylidene Dicamphor Sulfonic Acid;
Disodium Phenyl Dibenzimidazole Tetrasulfonate;
Methylene bis-Benzotriazolyl Tetramethylbutyiphenol;
Ethylhexyl triazone,
Bis-Ethylhexyloxyphenol Methoxyphenyl Triazine;
Diethylhexyl Butamido Triazone;
2,4,6-Tris(dineopentyl 4'-aminobenzalmalonate)-s-triazine;
2,4,6-Tris(diisobutyl 4'-aminobenzalmalonate)-s-triazine;
2,4,6-Tris(biphenyl-4-yl-1,3,5-triazine);
2,4,6-Tris(terphenyl)-1,3,5-triazine;
Drometrizole Trisiloxane;
Polysilicone-15;
Dineopentyl 4'-methoxybenzalmalonate
1,1-Dicarboxy-(2,2'-dimethylpropyl)-4,4-diphenylbutadiene;
2,4-Bis[5-1(dimethylpropyl)benzoxazol-2-yl-(4-phenyl)-imino]-6-(2-ethylhexyl)-imino-1,3,5-triazine;
and mixtures thereof.

17. The cosmetic/dermatological composition as defined by claim 14, comprising additional inorganic photoprotective agents selected from the group consisting of treated or untreated metal oxide pigments.

18. The cosmetic/dermatological composition as defined by claim 17, said pigments comprising treated or untreated titanium, zinc, iron, zirconium or cerium oxides and mixtures thereof.

19. The cosmetic/dermatological composition as defined by claim 1, further comprising at least one adjuvant selected from the group consisting of fatty substances, organic solvents, ionic or non-ionic, hydrophilic or lipophilic thickeners, demulcents, humectants, opacifiers, stabilizers, emollients, silicones, anti-foaming agents, fragrances, preservatives, anionic, cationic, non-ionic, zwitterionic or amphoteric surfactants, active agents, fillers, polymers, propellants and basifying or acidifying agents.

20. The cosmetic/dermatological composition as defined by claim 1, formulated as an oil-in-water or water-in-oil emulsion.

21. The cosmetic/dermatological composition as defined by claim 1, formulated as a product for the cosmetic treatment of the skin, lips, nails, hair, eyelashes, eyebrows and/or scalp.

22. The cosmetic/dermatological composition as defined by claim 1, formulated as a care product for the skin, lips, nails, hair and/or scalp.

23. The cosmetic/dermatological composition as defined by claim 1, formulated as a makeup product.

24. A process for improving the chemical stability with respect to UV radiation of at least one dibenzoylmethane compound UV-A screening agent, comprising formulating therewith an effective amount of at least one merocyanine sulfone compound of formula (1) as defined by claim 1.

25. A regime or regimen for photoprotecting a keratinous substrate against the damaging effects of UV-A radiation, comprising topically applying thereon a thus effective amount of the cosmetic/dermatological composition as defined by claim 1.

26. A regime or regimen for photoprotecting the skin, hair, lips, scalp, nails, eyelashes and/or eyebrows against the damaging effects of UV-A radiation, comprising topically applying thereon a thus effective amount of the cosmetic/dermatological composition as defined by claim 1.

* * * * *